United States Patent
Wendt et al.

(10) Patent No.: US 7,380,729 B2
(45) Date of Patent: Jun. 3, 2008

(54) DISPENSING METHOD

(75) Inventors: Oliver Wendt, Hamburg (DE); Hartwig Preckel, Hamburg (DE)

(73) Assignee: Evotec AG, Hamburg (DE)

( * ) Notice: Subject to any disclaimer, the term of this patent is extended or adjusted under 35 U.S.C. 154(b) by 193 days.

(21) Appl. No.: 10/542,436

(22) PCT Filed: Jan. 30, 2004

(86) PCT No.: PCT/EP2004/000823

§ 371 (c)(1),
(2), (4) Date: Dec. 22, 2005

(87) PCT Pub. No.: WO2004/067177

PCT Pub. Date: Aug. 12, 2004

(65) Prior Publication Data

US 2006/0202054 A1  Sep. 14, 2006

(30) Foreign Application Priority Data

Feb. 1, 2003 (DE) ................. 103 04 018

(51) Int. Cl.
*B05B 17/06* (2006.01)
*B05B 17/04* (2006.01)
*B05B 1/08* (2006.01)
*B05B 15/02* (2006.01)
*B65D 47/18* (2006.01)

(52) U.S. Cl. ............... 239/4; 239/102.1; 239/102.2; 239/112; 222/148; 222/420

(58) Field of Classification Search ............... 239/4, 239/102.1, 102.2, 112, 9, 104, 106; 222/148, 222/420, 1, 422; 422/100
See application file for complete search history.

(56) References Cited

U.S. PATENT DOCUMENTS

| 4,600,928 | A | * | 7/1986 | Braun et al. ............. 347/27 |
| 5,543,827 | A | * | 8/1996 | VanSteenkiste et al. ...... 347/27 |
| 6,203,759 | B1 | * | 3/2001 | Pelc et al. ............... 422/100 |
| 6,874,699 | B2 | * | 4/2005 | Larson et al. ............ 239/102.1 |
| 2001/0016177 | A1 | | 8/2001 | Pelc et al. ............... 422/100 |

FOREIGN PATENT DOCUMENTS

DE  3614960  11/1987
JP  2000028623  1/2000

OTHER PUBLICATIONS

International Search Report dated May 18, 2004 based on PCT application No. PCT/EP04/000823.

* cited by examiner

*Primary Examiner*—Darren W Gorman
(74) *Attorney, Agent, or Firm*—Ohlandt, Greeley, Ruggiero & Perle L.L.P.

(57) ABSTRACT

In a method for cleaning a liquid delivery device such as a dispensing or pipetting device, the liquid chamber can be flushed in a cleaning step. To remove gas bubbles which might exist in the liquid chamber, for example, the liquid in the liquid chamber is vibrated during the cleaning step.

8 Claims, 2 Drawing Sheets

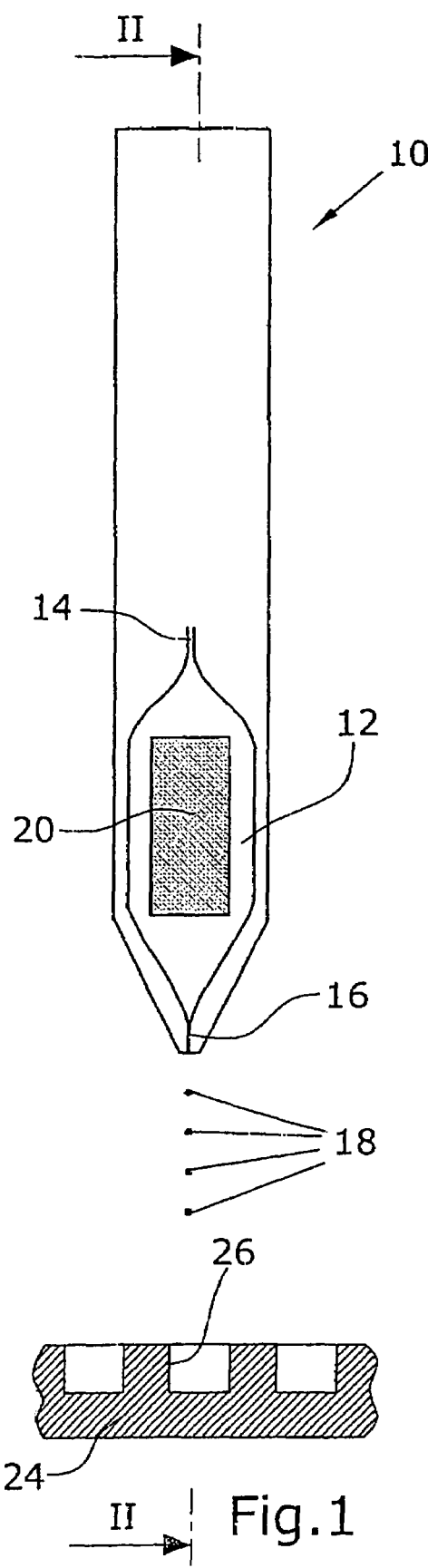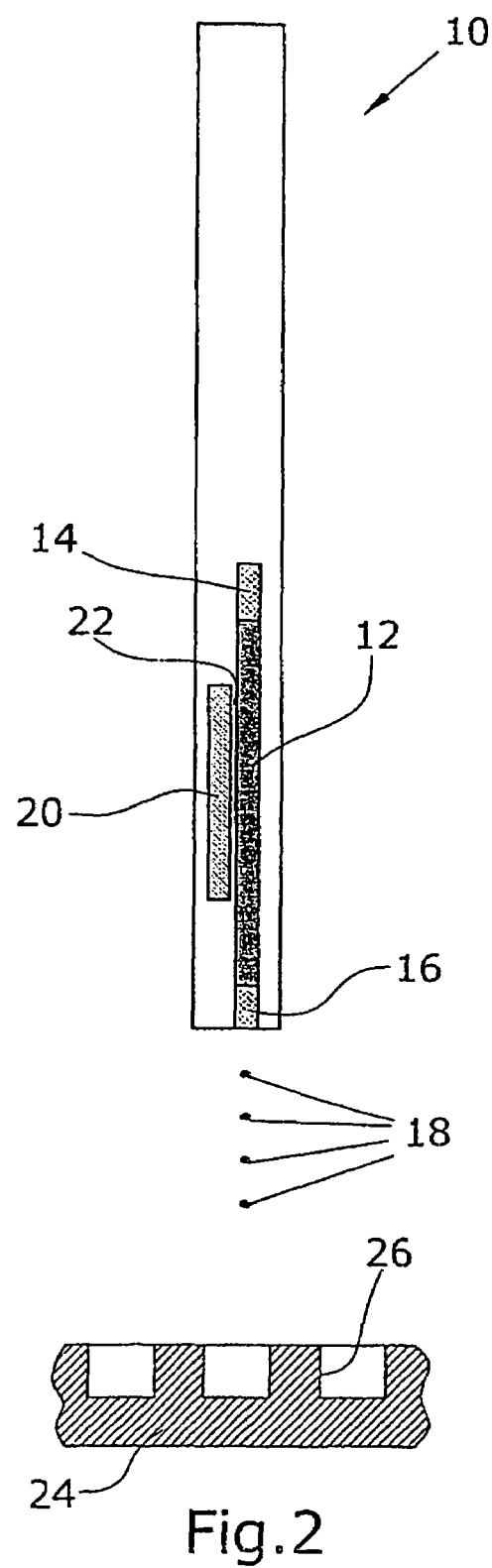

DISPENSING METHOD

FIELD OF THE INVENTION

The invention relates to a dispensing method for dispensing chemical and/or biological liquids in minimum amounts by means of a liquid delivery device, particularly a micropump in a dispensing and/or pipetting device and/or other microsystems.

DISCUSSION OF THE BACKGROUND ART

For dispensing and pipetting very small liquid amounts in the range of a few pl to µl, micropumps, for example, are utilized as a liquid delivery device, which eject drops through a nozzle of the dispensing or pipetting device. As a micropump, such dispensing or pipetting devices comprise a liquid chamber that contains a sample liquid or a system liquid. A wall of the sample chamber is configured to be, e.g., elastic, particularly as a diaphragm. A pulse generator such as a piezo actuator acts upon the elastic wall. Pressure pulses can be generated in the liquid chamber by the piezo actuator. They cause a delivery of liquid drops from the nozzle. The droplet volume is clearly defined so that the liquid amount delivered is clearly specified via the number of droplets. The volume of the individual drops is in the range of from 50-100 pl.

In principle, micropumps are very liable to fault. This is due to the very small dimensions and the sensitivity to precipitations and gaggings related thereto. Because of its compressibility, the presence of an air bubble, e.g., may result in that no delivery effect or a too small delivery effect occurs even if the diaphragm of the micropump is actuated. Furthermore, surface tension effects may impair the perfect function of such micropumps. Particularly with automation such as, for example, in medium or high throughput screening, a high reliability of such micropumps is required. Malfunctions which might nevertheless occur should be detected and repaired automatically. One problem which often occurs with micropumps, e.g., is that precipitations, e.g. of crystallizations of the liquid in the liquid chamber, are produced within the liquid chamber. Further, gas bubbles, particularly air bubbles, are often produced within the liquid chamber, a channel connected with the liquid chamber or the nozzle. This often results in a failure of the micropump. With micropumps used in dispensing and pipetting devices, gas bubbles at least lead to a falsification of the delivered drop size and thus to a falsification of the delivered liquid amount if they will not directly result in the failure of the micropump.

To avoid malfunctions in such liquid delivery devices, it is known to flush the liquid chamber with liquid in a cleaning step. The liquid in the liquid chamber, i.e., the sample or system liquid, is used for flushing. It is also possible to flush the chamber with flushing liquid via a separate connection of the liquid chamber with a reservoir. If necessary, the pump may be operated at an increased frequency or amplitude. Such known flushing methods, however, are time-consuming. This is particularly disadvantageous if such liquid delivery devices are used in medium or high throughput screening. Further, the liquid consumption in known flushing methods is extremely high. This is particularly disadvantageous when the flushing in a dispensing device has to be done with expensive sample liquid.

It is the object of the invention to provide a method for cleaning a liquid delivery device by means of which a quick and reliable cleaning is guaranteed.

SUMMARY OF THE INVENTION

In the method for dispensing chemical and/or biological liquids according to the invention, liquid is delivered in a dispensing step by means of a dispensing device. To this end, a pulse generator such as a piezo actuator acts upon a liquid chamber which contains the sample liquid to be delivered. The pulse generator generates a pressure pulse in the liquid chamber so that a liquid droplet is delivered through a capillary channel. During a dispensing step, several droplets, preferably at least 5, at least 10 in a particularly preferred manner, and at least 20 droplets in particular are delivered. Particularly, up to 500, if necessary, even up to 1,000 droplets, can be delivered in a dispensing step. The number of the droplets delivered corresponds with the number of pulses of the pulse generator so that the delivered liquid amount can be directly defined since the volume of the individual droplet is known.

Before or after such a dispensing step, a cleaning step is performed according to the invention, wherein flushing liquid is passed through the liquid chamber. Sample liquid can also be used as a flushing liquid.

According to the invention, the medium in the liquid chamber of the liquid delivery device, i.e., particularly the liquid and existing impurities, are vibrated during the cleaning step in which the liquid chamber is flushed. By vibrating the medium, it is possible to act upon impurities, particularly gas bubbles, existing in the liquid chamber in such a manner that they disintegrate. Impurities which may be both particles and gas bubbles disintegrate into smaller parts and smaller bubbles, respectively. These can be flushed out of the liquid chamber more easily. Thereby, for example, a gagging of the nozzle because of relatively large impurities is avoided if the liquid delivery device is a dispensing or pipetting device. By vibrating the medium located in the liquid chamber and the disintegration of the impurities, particularly the gas bubbles, caused thereby, they can be flushed out of the liquid chamber more easily. The method according to the invention is particularly suitable for flushing out gas bubbles which cannot be flushed out or only difficulty so by means of known flushing methods since gas bubbles adhere to the surfaces of the dispensing device. Thus, the liquid chamber can be cleaned faster. This is a particular great advantage with automatic methods such as the medium or high throughput screening. Thus, it is possible by means of the method according to the invention to considerably reduce the cleaning times. Further, the reliability is increased by the method according to the invention since larger impurities disintegrate and c an thus be reliably removed from the liquid chamber. Furthermore, the consumption of liquid in a cleaning step is considerably reduced. This is particularly advantageous with dispensing devices in which the cleaning is effected by means of sample liquid.

In a particularly preferred embodiment of the invention, the frequency of the vibrations occurring in the liquid is varied during a cleaning step. To this end, the frequency of a pulse generator acting upon the liquid is varied, the variation of the frequency of the pulse generator provoking a variation of the vibration frequency of the medium. It is particularly preferred if a piezo actuator or a corresponding component is used as a pulse generator to this end. If the liquid delivery device is a dispensing or pipetting device, it is particularly preferred to use the pulse generator such as, for example, the piezo actuator, by which the drop delivery is caused, as a pulse generator for generating the vibrations in the liquid as well. This has the advantage that no additional component is required to perform the cleaning step including the flushing of the liquid chamber and the vibrating of the medium according to the invention.

Varying the vibrational frequency has the advantage that impurities or gas bubbles of different sizes can be resonated whereby the disintegration process is triggered. Thus, varying the frequency results in a further reduction of the flushing times. This increases the reliability of the liquid delivery device and reduces the liquid amount required for flushing. This is particularly advantageous with medium and high throughput screening. The frequency or the different frequencies which are produced during a cleaning step can be advantageously selected, for example, in dependence on the used liquid and the danger of larger or smaller agglomerates resulting therefrom, for example. The frequencies can also be matched to the fact that a liquid has a stronger or weaker tendency to develop gas and thus forms gas bubbles.

Experiments have shown that a minimum frequency of at least 1 kHz, preferably at least 3 kHz, is particularly advantageous when gas bubbles occur. Very good results can further be achieved when the maximum frequency amounts to 60 kHz at maximum, preferably 40 kHz at maximum. Within the minimum frequency and the maximum frequency, the frequency is changed continuously or stepwise. Good cleaning results can be achieved when the frequency is increased stepwise by 200-250 Hz per step. Starting from a minimum frequency, the frequency is preferably increased toward the maximum frequency. Since larger bubbles disintegrate into smaller and smaller bubbles and particles disintegrate into smaller and smaller particles, respectively, it is advantageous to increase the frequency to a maximum frequency starting from the minimum frequency for the disintegration into bubbles or particles which are as small as possible and adapted to be flushed out can be accelerated. If necessary, changes between individual frequencies are possible so that the frequencies are repeatedly increased and decreased during one cleaning step. Furthermore, a combination of both processes is possible.

BRIEF DESCRIPTION OF THE DRAWINGS

Hereinafter, the invention is explained in detail with respect to a preferred embodiment with reference to the accompanying drawings.

FIG. 1 is a schematic front view of a liquid delivery device,

FIG. 2 is a schematic sectional view along the line II-II in FIG. 1,

DETAILED DESCRIPTION OF THE PREFERRED EMBODIMENT

Figure 3:
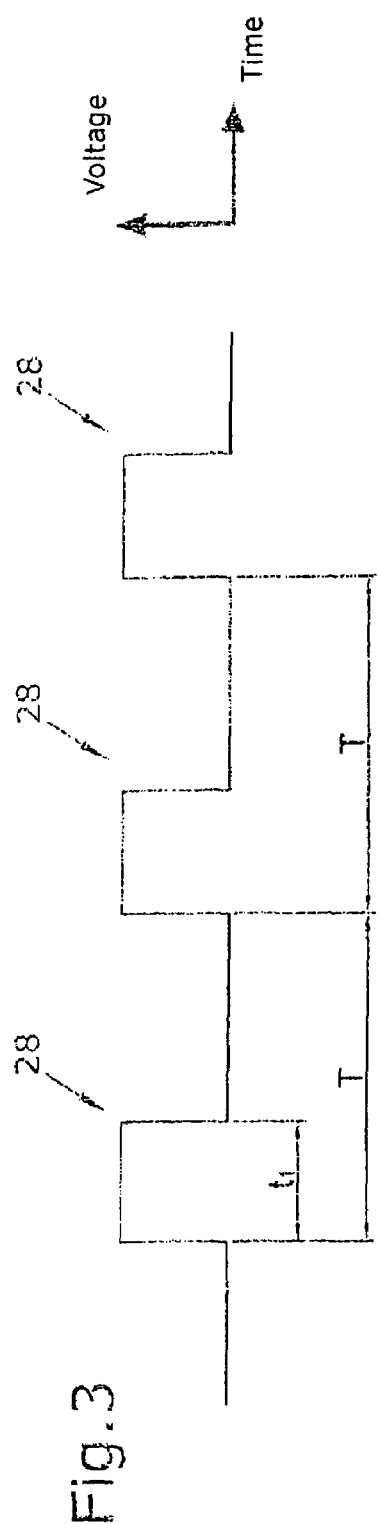
FIG. 3 is an example of an excitation signal for exciting piezo actuators.

The liquid delivery device 10 illustrated in FIGS. 1 and 2 is, e.g., a dispensing device. It comprises a liquid chamber 12 connected with a reservoir via a channel 14. In a dispensing device, the reservoir contains the sample liquid dispensed in the form of drops 18 through a nozzle or the capillary channel 16. If necessary, the liquid chamber 12 is further connected with another reservoir containing flushing liquid for performing a cleaning step. A piezo actuator 20 acts upon the liquid in the liquid chamber 12. The piezo actuator 20 acts upon an elastic wall 22 of the liquid chamber 12. By applying a voltage to the piezo actuator 20, the elastic wall 22 is deformed and a pressure pulse is exerted upon the liquid in the liquid chamber 12. Thereby, a drop 18 is delivered, e.g., toward a microtiter plate 24 for filling wells 26 located in the microtiter plate 24.

The excitation pulse form shown in FIG. 3 is a possible voltage pulse sequence applied to the piezo actuator 20 during the dispensing step for producing droplets 18.

Over a time period $t_1$, the square pulse illustrated in FIG. 3 produces a voltage applied to the piezo actuator 20, which is repeated after a period T. By each excitation pulse 28, a droplet 18 is delivered. Instead of a square pulse, a trapezoidal pulse, for example, or a square pulse with an obliquely falling edge, for example, can be used as well. It is also possible to apply polygonal pulses to the piezo actuator 20, a voltage pointing to the opposite direction being applied before or after the excitation pulse 28, if necessary. Further, it is also possible, for example, to apply sinusoidal excitation pulses to the piezo actuator 20 or another pulse generator.

Figure 4:
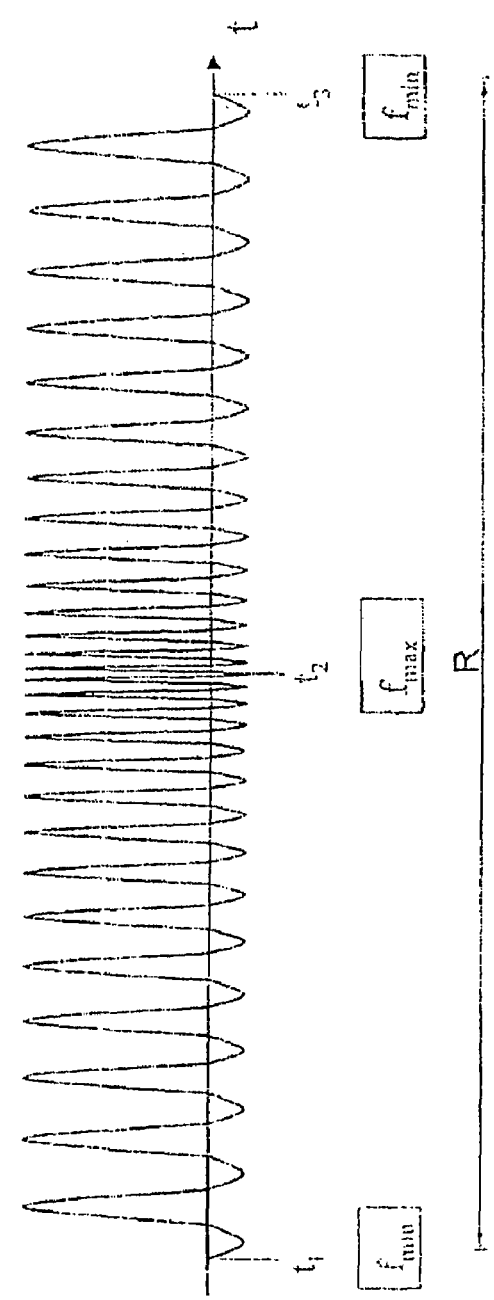
FIG. 4 shows a frequency course according to the invention during a cleaning step.

During a cleaning step R (FIG. 4) performed before or after the dispensing step, an excitation frequency that is, e.g., sinusoidal, is applied to the piezo actuator 20. The frequency may be continuously increased, e.g., from a minimum frequency $f_{min}$ at a time $t_1$ up to a maximum frequency $f_{max}$ at a time $t_2$. After the time $t_2$, the frequency is then reduced continuously down to a minimum frequency $t_{min}$ until a time $t_3$. During such a continuous or perhaps stepwise variation of the frequency, preferably more than 50, preferably more than 80 and particularly preferably more than 120 vibration periods are produced. This is preferably effected per frequency step.

A cleaning step according to the invention can be particularly performed after a fault has been detected. If necessary, it is also additionally possible to preventively perform a cleaning step, at predetermined intervals, for example, or after defined operational situations. It is possible, but not required, to perform a cleaning step R before or after each dispensing step.

What is claimed is:

1. A dispensing method for dispensing chemical and/or biological liquids in minimum amounts, wherein
   in a dispensing step, several droplets are delivered by a dispenser by a pulse generator acting upon a liquid chamber to deliver droplets through a capillary channel, and,
   in a cleaning step, flushing liquid is passed through the liquid chamber,
   wherein, during the cleaning step, the medium in the liquid chamber is vibrated in order to destroy impurities, and
   wherein a frequency of the vibrations is varied during said cleaning step.

2. The method according to claim 1, wherein the vibrations are generated by the pulse generator acting upon an elastic wall of the liquid chamber.

3. The method according to claim 2, wherein the frequency of the pulse generator is varied during said cleaning step.

4. The method according to claim 1, wherein the frequency is selected such that impurities disintegrate.

5. The method according to claim 1, wherein a minimum frequency ($f_{min}$) during said cleaning step amounts to at least 1 kHz.

6. The method according to claim 1, wherein a maximum frequency ($f_{max}$) during said cleaning step amounts to 60 kHz at maximum.

7. The method according to claim 1, wherein the frequency is increased stepwise from a minimum frequency ($f_{min}$) and/or is decreased stepwise from a maximum frequency ($f_{max}$).

8. The method according to claim 1, wherein, during the dispensing step, the pulse generator is operated with an excitation pulse serving to deliver droplets.

* * * * *